United States Patent [19]

Forward et al.

[11] 4,193,988
[45] Mar. 18, 1980

[54] ORAL HYGIENE COMPOSITIONS

[75] Inventors: Geoffrey C. Forward, Epsom Downs; Janet A. Gawthorpe, nee Baylis, Orpington, both of England

[73] Assignee: Beecham Group Limited, Great Britain

[21] Appl. No.: 924,001

[22] Filed: Jul. 12, 1978

Related U.S. Application Data

[63] Continuation-in-part of Ser. No. 493,717, Aug. 1, 1974, abandoned, which is a continuation of Ser. No. 369,451, Jun. 13, 1973, abandoned, which is a continuation of Ser. No. 247,948, Apr. 27, 1972, abandoned.

[30] Foreign Application Priority Data

Apr. 29, 1971 [GB] United Kingdom .............. 12099/71
Dec. 14, 1971 [GB] United Kingdom .............. 58064/71

[51] Int. Cl.$^2$ ................................................ A61K 7/18
[52] U.S. Cl. .......................................... 424/52; 424/57
[58] Field of Search ................................... 424/52, 57

[56] References Cited

FOREIGN PATENT DOCUMENTS 2221023 11/1972 Fed. Rep. of Germany .
572352 10/1945 United Kingdom .
1009957 11/1965 United Kingdom .
1222197 2/1971 United Kingdom .

OTHER PUBLICATIONS

Fedorov, Yu. A. (Translation) Stomatologiya Moscow (1969) 48(5) 15-19 as abstracted in Chem. Abstr. 72 #99012b (1970).
Fedorov, Yu. A., Vop, Stomatol. Mater. Sovmestnoi Nauch. Sess. Odess. Sofii Nauch–Issled. Inst. Stomatol. 1965 (pub. 1970): 10–18 as abstracted in Chem. Abstr. 79 #100720j (1973).

*Primary Examiner*—Shep K. Rose
*Attorney, Agent, or Firm*—Jacobs & Jacobs

[57] ABSTRACT

Oral hygiene compositions particularly in the form of dentifrices, having an enhanced effect in reducing the solubility of dental enamel and which compositions are made up of sodium monofluorophosphate as anti-caries agent in potentiating combination with calcium glycerophosphate, the sodium monofluorophosphate and calcium glycerophosphate being present in the composition in the weight ratio of 10:1 to 3:1. The oral hygiene composition is in the form of a powder, paste, gel or liquid.

5 Claims, No Drawings

ORAL HYGIENE COMPOSITIONS

This application is a continuation in part of appplication Ser. No. 493,717 filed Aug. 1, 1974 which is a continuation of application Ser. No. 369,451 filed June 13, 1973, which in turn is a continuation of application Ser. No. 247,948 filed Apr. 27, 1972 all now abandoned.

This invention relates to oral hygiene compositions having anti-cariogenic activity and more particularly to anti-caries dentifrices.

In the past few years many proposals have been made to incorporate various fluoride compounds into oral hygiene compositions such as dentifrices in order to provide them with anti-cariogenic activity. A particular fluoride that has found favour for this purpose is sodium monofluorophosphate, though the use of other water-soluble monofluorophosphates has also been proposed. An important effect of these monofluorophosphates is the fact that the solubility of tooth enamel in weakly acid media is reduced.

We have now further found that the activity of sodium monofluorophosphate in reducing the solubility of tooth enamel is enhanced or potentiated when used in admixture with certain proportions of calcium glycerophosphate. These results are surprising because we have shown, for example, that there is no potentiation when sodium glycerophosphate is used in conjunction with sodium monofluorophosphate. Moreover, we have also shown that there is no potentiation of the solubility-reducing properties of the monofluorophosphate when this is used in conjunction with inorganic calcium salts such as calcium chloride.

Accordingly, the present invention provides an anti-cariogenic oral hygiene composition which enhances reduction of solubility of dental enamel wherein the anti-caries agent is 0.08 to 7.6% by weight of sodium monofluorophosphate in potentiating combination with calcium glycerophosphate, the sodium monofluorophosphate and calcium glycerophosphate being present in the composition in the weight ratio of 10:1 to 3:1.

The sodium monofluorophosphate is water soluable and may contain impurities such as sodium fluoride or water-soluble sodium phosphate. These are not deleterious, but the sodium monofluorophosphate employed should have a total fluoride content of above 12%, preferably above 12.7%; a content of not more than 1.5%, preferably not more than 1.2%, of free sodium fluoride; and a sodium monofluorophosphate content of at least 12%, preferably at least 12.1%, all calculated as fluorine.

The inclusion of calcium glycerophosphate in dentifrices is disclosed in British Pat. No. 572,352 but with no reference to the concomitant presence of sodium monofluorophosphate.

Accordingly, potentiation of sodium monofluorophosphate by calcium glycerophosphate has not hitherto been appreciated or suggested.

The calcium glycerophosphate or calcium phytate is present in the compositions of the invention in an amount such that the weight ratio of sodium monofluorophosphate to the total calcium glycerophosphate present is within the range of 10:1 to 3:1.

Preferably, the amount of sodium monofluorophosphate is 0.8% and the calcium glycerophosphate is 0.2% by weight of the composition.

The oral hygiene compositions of the invention are often in the form of dentifrices and these will also usually contain polishing agents, surfactants, gelling agents and other excipients such as flavouring and colouring agents. The compositions may be in the form of powders, pastes or liquids. A particularly useful form of composition is one in the form of a dentifrice gel.

The polishing agent may be selected from those currently employed for this purpose in dental preparations. For instance, there may be used water-insoluble sodium or potassium metaphosphate, hydrated or anhydrous dicalcium phosphate, calcium pyrophosphate, zirconium silicate or mixtures thereof. Particularly useful polishing agents are various forms of silica, especially silica xerogels as described in U.S. Pat. No. 3,538,230. The polishing agent is generally finely divided with a particle size smaller that 10 microns, preferably of between 2 and 6 microns. The polishing agent may be employed in an amount of from 10 to 99% by weight of the dentifrice. Preferably the dentifrice compositions are in the form of pastes containing 20 to 75% of the polishing agent, though these can be in the form of powders containing 70 to 99% of the polishing agent.

A suitable surfactant is normally included in the dentifrice compositions, preferably this being a water-soluble non-soap synthetic organic detergent. Suitable detergents are the water-soluble salts of: higher fatty acid monoglyceride monosulphates (for example sodium hydrogenated coconut fatty acid monoglyceride monosulphate); higher alkyl sulphates (for example sodium lauryl sulphate); alkylarylsulphonates (for example sodium dodecylbenzenesulphonates); and higher alkyl sulphoacetates (for example sodium lauryl sulphoacetate).

There may also be used the saturated higher aliphatic acyl amides of lower aliphatic amino carboxylic acids having 12 to 16 carbon atoms in the acyl radical and in which the amino acid portion is derived from the lower aliphatic saturated monoaminocarboxylic acids having 2 to 6 carbon atoms, such as the fatty acid amides of glycine, sarcosine, alanine, 3-aminopropanoic acid and valine, particularly the N-lauryl, myristoyl and palmitoyl sarcosinate compounds. Conventional non-ionic surfactants may also be included if desired.

The surface-active materials are generally present in an amount of 0.05 to 10%, preferably 0.5 to 5% by weight of the dentifrice composition.

The tooth powders and pastes are prepared in the usual manner. Thus the constituents can be mixed in the dry state or as slurries or solutions. It is often advantageous to employ the glycerophosphate in the form of an aqueous solution.

In general the liquids in the dental cream or paste will comprise chiefly water, glycerol, sorbitol or propylene glycol, including suitable mixtures thereof. It is advantageous usually to use a mixture of water and glycerol, preferably in combination with sorbitol. A gelling agent such as the natural and synthetic gums and gum-like materials, preferably Irish Moss or sodium carboxymethycellulose, may be used. Other gums which may be used are gum tragacanth, polyvinylpyrrolidone and starch. They are usually used in an amount up to 10%, preferably 0.5 to 5% by weight of the toothpaste.

The pH of the dental cream or an aqueous slurry of the tooth powder is substantially neutral such as a pH of about 6 to 8. If desired, a small amount of acid such as citric acid or an alkaline material may be added.

Other materials may be added such as soluble saccharin, flavouring oils (e.g. oils of spearmint, peppermint, wintergreen), colouring or whitening agents (e.g. titanium dioxide), preservative (e.g. sodium benzoate), emulsifying agents, acidifying agents (e.g. citric acid), silicones, alcohol, menthol and chlorophyll compounds (e.g. sodium copper chlorophyllin).

The compositions of the invention may also be in the form of other oral hygiene compositions, for example, the sodium monofluorophosphate and calcium glycerophosphate ingredients may be incorporated in mouth washes, which can be of the suspension type, or in compositions which will be chewed by the user, for example, chewing gum, tablets, pastilles and lozenges. These compositions will contain the conventional base materials together with suitable flavouring and sweetening agents.

The compositions of the invention are illustrated by the following Examples in which quantities are expressed on a weight basis.

|  | Examples | | | |
|---|---|---|---|---|
|  | 1 | 2 | 3 | 4 |
| Chalk | 49.0 | 49.0 | 47.9 | 47.9 |
| Dicalcium Phosphate Dihydrate | — | — | — | — |
| Silica Xerogel (Syloid 74) | — | — | — | — |
| Pyrogenic Silica (Aerosil 200) | — | — | — | — |
| Glycerol | 13.0 | 13.0 | 26.0 | 26.0 |
| Sorbitol (70% Solution) | 13.0 | 13.0 | — | — |
| Magnesium Aluminium Silicate | 0.75 | 0.75 | 0.75 | 0.75 |
| Calcium Silicate | — | — | 0.2 | 0.2 |
| Sodium Carboxymethyl Cellulose | 1.0 | 1.0 | 0.9 | 0.9 |
| Sodium Lauryl Sulphate | 1.5 | 1.5 | 1.15 | 1.15 |
| Sodium Monofluorophosphate | 0.8 | 0.8 | 0.8 | 0.8 |
| Calcium Phytate | 0.5 | 0.1 | 0.1 | — |
| Calcium Glycerophosphate | — | — | — | 0.2 |
| Saccharin | 0.2 | 0.2 | 0.1 | 0.1 |
| Anticorrosive | 0.5 | 0.5 | — | — |
| Flavour | q.s. | q.s. | q.s. | q.s. |
| Water | to 100% | to 100% | to 100% | to 100% |

|  | Examples | | | |
|---|---|---|---|---|
|  | 5 | 6 | 7 | 8 |
| Chalk | 49.0 | — | 11.0 | 6.5 |
| Dicalcium Phosphate Dihydrate | — | — | — | 4.0 |
| Silica Xerogel (Syloid 74) | — | 14.0 | — | — |
| Pyrogenic Silica (Aerosil 200) | — | — | — | 2.5 |
| Glycerol | 13.0 | 30.0 | 50.0 | 50.0 |
| Sorbitol (70% Solution) | 13.0 | 43.0 | 14.0 | 14.0 |
| Magnesium Aluminium Silicate | 0.75 | — | — | — |
| Calcium Silicate | — | — | — | — |
| Sodium Carboxymethyl Cellulose | 1.0 | 0.8 | 0.8 | 0.55 |
| Sodium Lauryl Sulphate | 1.5 | 1.5 | 1.5 | 1.5 |
| Sodium Monofluorophosphate | 0.8 | 0.8 | 0.8 | 0.8 |
| Calcium Phytate | — | — | 0.2 | — |
| Calcium Glycerophosphate | 0.2 | 0.2 | — | 0.2 |
| Saccharin | 0.2 | q.s. | q.s. | q.s. |
| Anticorrosive | 0.5 | — | — | — |
| Flavour | q.s. | q.s. | q.s. | q.s. |
| Water | to 100% | to 100% | to 100% | to 100% |

Syloid and Aerosil are Registered Trade Marks

The efficacy of these formulations is shown, for example, by tests carried out on the composition of Example 3. Discs of hydroxyapatite were prepared by blending it with 7.5% of polyethylene to improve binding characteristics followed by moulding separate discs by compression at 5000 kg. for one minute and subsequent heating to 160° C. Separate discs were treated with a slurry of the dentifrice of Example 3 with water (water:dentifrice=2:1) using a brushing apparatus for one minute. Some of the discs were then stored for two days in a humid atmosphere. Comparative discs were treated in which the dentifrice composition omitted the calcium phytate. The treated discs were each placed beneath a rotating propeller in acetic acid buffer at pH 4.65 and 37° C. for one hour. The percentage solubility reduction relative to treatment with an identical dentifrice but containing no fluorophosphate or organic phosphate was determined in each case as with the preceding experiments. The results are set out in Table I.

Table I

| Composition | Solubility Reduction Achieved | |
|---|---|---|
|  | Immediate Dissolution | Dissolution after storage |
| Example 3 | 8.5% | 12.5% |
| Comparative Example without calcium phytate | 3.5% | 9.0% |

Similar experiments were carried out using the composition of Examples 3 and 4, but the discs were compressed at 10,000 kg. and 110° C. and treated with a slurry of concentration, water:dentifrice=1:1 for two minutes. Only immediate dissolution tests were performed. The results are given in Table II.

Table II

| Composition | No. of tests | Solubility Reduction Achieved |
|---|---|---|
| Example 3 | 3 | 32% |
| Example 4 | 3 | 26% |
| Comparative Example without organic Phosphate | 3 | 13% |

EXAMPLES 9-10

Compositions 9 and 10 were prepared respectively as for Example 7 but with the amount of calcium phytate being reduced to 0.1% (Example 9) and with the calcium phytate being replaced by 0.2% calcium glycerophosphate (Example 10). Tests were performed as for Table II with 1 and 2 minutes of application of the dentifrice slurry to the disc. The results obtained are given in Table III wherein the comparative composition omitted entirely the organic phosphate.

Table III

| Composition | Time of Application (mins.) | Solubility Reduction Achieved |
|---|---|---|
| 9 | 2 | 26.0% |
| 10 | 2 | 27.4% |
| Comparative | 2 | 13.0% |
| 10 | 1 | 10.0% |
| Comparative | 1 | 3.0% |

We claim:

1. In a method of enhancing reduction of solubility of dental enamel by an anti-cariogenic oral hygiene composition, the steps of preparing an anti-cariogenic oral hygiene composition having a potentiating combination of sodium monofluorophosphate and calcium glycerophosphate in a weight ratio of 10:1 to 3:1, the sodium monofluorophosphate being present in an amount of 0.08% to 7.6%, by weight, and contacting the dental enamel with the composition.

2. A method according to claim 1 in which the sodium monofluorophosphate and calcium glycerophosphate are combined in the weight ratio of about 8:1.

3. A method according to claim 1 in which the composition is formulated in powder, paste, gel or liquid form.

4. A method according to claim 1 in which the sodium monofluorophosphate is present in the amount of 0.8% and the calcium glycerophosphate is present in the amount of 0.2%, both calculated on the weight of the composition.

5. A method according to claim 1 in which the composition is in the form of a dentifrice paste having therein 0.005 to 10%, by weight, of the composition of a water-soluble non-soap synthetic organic detergent.

* * * * *